US008303941B2

(12) United States Patent (10) Patent No.: US 8,303,941 B2
Musumeci (45) Date of Patent: Nov. 6, 2012

(54) CHELATED MINERAL WATER

(75) Inventor: Stephen Musumeci, Cresco, PA (US)

(73) Assignee: Geologix, Inc., Birmingham, MI (US)

( * ) Notice: Subject to any disclaimer, the term of this patent is extended or adjusted under 35 U.S.C. 154(b) by 171 days.

(21) Appl. No.: 12/596,603

(22) PCT Filed: Apr. 19, 2008

(86) PCT No.: PCT/US2008/005092
§ 371 (c)(1),
(2), (4) Date: Oct. 19, 2009

(87) PCT Pub. No.: WO2008/140665
PCT Pub. Date: Nov. 20, 2008

(65) Prior Publication Data
US 2010/0166682 A1 Jul. 1, 2010

Related U.S. Application Data

(60) Provisional application No. 60/912,994, filed on Apr. 20, 2007.

(51) Int. Cl.
*A61K 8/18* (2006.01)
*A61K 33/00* (2006.01)
*A61K 33/06* (2006.01)
*A61K 33/04* (2006.01)
*A61Q 1/10* (2006.01)

(52) U.S. Cl. ............ 424/59; 424/600; 424/607; 424/62; 424/63; 424/64; 424/646; 424/683; 424/701; 424/709

(58) Field of Classification Search ............ 424/59, 424/682, 646, 709, 600, 607, 401, 49, 62, 424/63, 64, 701, 70–7, 70.1
See application file for complete search history.

(56) References Cited

U.S. PATENT DOCUMENTS

| 6,372,198 | B1 * | 4/2002 | Abbate | 424/49 |
| 6,649,176 | B1 * | 11/2003 | Shapiro et al. | 424/401 |
| 2002/0142019 | A1 * | 10/2002 | Kuhnau | 424/401 |
| 2006/0204452 | A1 * | 9/2006 | Velamakanni et al. | 424/49 |

* cited by examiner

*Primary Examiner* — Blessing Fubara
(74) *Attorney, Agent, or Firm* — Gifford, Krass, Sprinkle, Anderson & Citkowski, P.C.

(57) ABSTRACT

A composition comprising mineral water and a chelating agent present in an amount sufficient to maintain all of the minerals in the water in solution. The mineral water is preferably obtained from Mount Clemens, Mich., US, and is preferably chelated with an ammonium and/or a sodium salt of an acid selected from the group consisting of ethylenediaminetetraacetic acid, nitrilotetraacetic acid, β-alaninediacetic acid, ethylenediaminosuccinic acid, aminotrimethylenephosphoric acid, serinediaacetic acid, asparaginediacetic acid, methylgylcinediacetic acid and mixtures thereof. The resultant chelated mineral water may be combined with a cosmetically acceptable skin-conditioning agent and a cosmetically acceptable topical carrier, thereby resulting in a cosmetic composition that will confer beneficial effects on the skin, e.g., softening, hydrating and healing effects.

38 Claims, No Drawings

CHELATED MINERAL WATER

CROSS-REFERENCE TO RELATED APPLICATION

This application is the U.S. National Stage of Application No: PCT/US2008/005092 filed Apr. 19, 2008, and which claims the benefit of U.S. Provisional Application Ser. No. 60/912,994 filed Apr. 20, 2007. The entire contents of both applications are hereby incorporated by reference in their entirety into this application.

FIELD OF THE INVENTION

The invention relates to cosmetic compositions for the treatment of skin. More particularly, the invention relates to skin-treatment cosmetic compositions containing a mineral water and a chelating agent present in an amount to maintain the minerals in the water in solution. A preferred mineral water is that obtained from Mount Clemens, Mich., US.

BACKGROUND OF THE INVENTION

The human body requires nearly two-thirds of all the elements currently identified by science to maintain proper health. Balancing these minerals is a vital yet complex task. The skin is responsible for maintaining body temperature and excreting waste. The appearance of the skin is a diagnostic tool used by medical professionals and patients alike because it is an indicator of how effectively the body is ridding itself of waste and impurities.

If the body does not receive enough minerals, the skin will be affected. Minerals are components of the bones, teeth, soft tissue, muscle, blood and nerve cells—all vital to overall mental and physical well-being. Dry skin may indicate a mineral deficiency, prohibiting cells from properly retaining moisture.

The skin's mineral balance can be attributed to both minerals ingested and those applied to the skin's surface. For thousands of years, man has utilized the natural resources of minerals from hot springs and mineral baths to increase the mineral content of the skin. Mineral baths work on the principle of drawing toxins from the body while restoring the body's natural mineral balance. From springs across North America to the Dead Sea, bathing in such springs has been used to infuse the skin with nutrients. Topically applied nutrients can also act locally on the surface of the skin to enhance tissue repair and wound handling.

Some mineral waters may have beneficial effects on the skin, e.g., softening, hydrating and healing effects. These various effects are a result of the minerals found in the water, acting singly or in combination. Not all mineral waters have such beneficial effects and of those that do, the nature and strength of the effects will vary depending upon the particular mineral composition.

Mineral water compositions can have stability problems resulting from the interaction of the various mineral species with atmospheric oxygen, other atmospheric gases or with other materials present in the mineral water composition. Such stability problems can cause the formation of precipitates, the generation of off-colored species, the generation of odorous species and chemical reactions, which can change the composition of the mineral water.

OBJECTS OF THE INVENTION

A principal object of the invention is to provide an agent that will stabilize the component of the mineral water and prevent the formation of precipitates or other unwanted species.

A further object of the invention is to provide a cosmetic composition containing the stabilized mineral water such that the resultant cosmetic composition will provide beneficial effects, e.g., hydration, softening, healing, etc. upon topical application of the cosmetic composition to the skin.

An additional object of the invention is to provide for the restoration and preservation of skin cells by using natural substances.

SUMMARY OF THE INVENTION

The invention relates to a chelated mineral water, i.e., a mineral water containing a chelating agent that will prevent the formation of precipitates and other unwanted species upon exposure of the mineral water to the atmosphere. The invention also relates to cosmetic compositions containing such chelated mineral water and other cosmetically acceptable ingredients such that the compositions will provide beneficial effects upon application to the skin. It appears that when the cosmetic compositions of the invention are topically applied to the skin, the compositions can enhance the uptake of oxygen, water and nutrients into the skin (i.e., the skin cells), enhance skin cell metabolism, reduce the loss of skin firmness and elasticity and have a reduced incidence of eye irritation.

DETAILS OF THE INVENTION

In one embodiment, the invention is directed to a mineral water composition containing a chelating agent present in an amount sufficient to maintain all of the minerals in the water in solution (such composition is hereinafter referred to as a "chelated mineral water"). Preferably, the mineral water is obtained from Mount Clemens, Mich., US. However any other naturally occurring or synthesized mineral water having the minerals described below are also within the purview of this invention.

In another embodiment, a cosmetic composition is prepared from ingredients comprising the chelated mineral water and a cosmetically acceptable monomeric or polymeric skin-conditioning agent and a cosmetically acceptable topical carrier.

Preferably, the minerals in the mineral water are of cations that include calcium, magnesium, iron, potassium and sodium and mixtures thereof, and of anions that include chloride, sulfate, bromide and mixtures thereof. Typically, the foregoing cations and anions will be present in the mineral water in the following amounts on the basis of grams per liter of water: calcium: about 5 to about 20; magnesium: about 2 to about 6; potassium: about 0.5 to about 3; iron: about 1 to about 4; sodium: about 0.1 to about 0.3; chloride: about 50 to about 200; sulfate: about 1 to about 2; and bromide: about 0.4 to about 0.8. In general, the mineral water will have a mineralization of about 10-30 wt. % of the foregoing cations and anions.

Typically, the chelating agent will be an ammonium and/or a sodium salt of an acid that may be ethylenediaminetetraacetic acid, nitrilotetraacetic acid, β-alaninediacetic acid, ethylenediaminosuccinic acid, aminotrimethylenephosphoric acid, serinediaacetic acid, asparaginediacetic acid, methylglycinediacetic acid and mixtures thereof. Preferably, the chelating agent comprises an ammonium and/or a sodium salt of ethylenediaminetetraacetic acid, e.g., a mixture of the disodium and the tetra sodium salts of ethylenediaminetetraacetic acid or a mixture of the ammonium, disodium and tetrasodium salts of ethylenediaminetetraacetic acid. In general, the chelating agent will be employed in an amount of about 0.01 to about 20.0 wt. %, preferably 0.5 to 5.0 wt. %, based on the weight of the chelated mineral water.

It is preferred that the chelated mineral water contains less than about 1 ppm of mercury or other heavy metals, less than about 1 ppm of cyanide, less than about 1 ppm of nitrite-nitrate and less than about 1 ppm of phenolics.

When formulating a cosmetic composition containing the chelated mineral water of the invention, the composition will typically include one or more of the following skin-conditioning ingredients: an emollient; a lipid material such as a shea butter extract; a film-former; an emulsifier such as a stearate; a humectant; a solvent; an optional co-solvent; a cationic surfactant; an anionic surfactant; an amphoteric surfactant; a zwitterionic surfactant; a cationic phospholipid; a hair-conditioning agent; an anti-inflammatory agent; a skin moisturizer; a skin exfoliant; a skin cleanser; a skin protectant; a silicone; a skin-soothing agent; a skin penetration agent; a skin-whitening agent; a solubilizing agent; an anesthetic; an analgesic; a hydroxy acid; an essential amino acid and/or an ester or salt thereof; an essential fatty acid and/or an ester or salt thereof; a hormone; a colorant and/or a dye; a thickener; a rheology control agent; a preservative; an insect repellant; a vitamin and/or pro-vitamin; a perfume and/or a fragrance; a plant extract; a flavorant; seed; crushed seed nut shells; silica; a clay; mica; beads; luffa particles; polyethylene balls; a pH adjusting agent; a processing flow agent; and mixtures thereof.

In general, the cosmetic composition will contain about 0.5 to about 76 wt. % of the chelated mineral water, based upon the weight of the cosmetic composition. The remainder of the cosmetic compositions will comprise the cosmetically acceptable carrier and one or more one or more of the ingredients recited above.

The cosmetically acceptable carriers for use in formulating the cosmetic compositions of the invention comprise an aqueous and/or organic solvent. Suitable organic solvents include propylene glycol, polyethylene glycol (200-600), polypropylene glycol (425-2025), glycerol, 1,2,4-butanetriol, sorbitol and esters thereof, 1,2,6-hexanetriol, ethanol, isopropanol, butanediol and mixtures thereof.

Preferred ingredients for inclusion in the cosmetic compositions of the invention include butylated hydroxyanisole, butylated hydroxytoluene, propyl gallate, tert.-butylhydroquinone, ascorbyl palmitate, capsaicin, reserbatol, linolenic acid, γ-linolenic acid, linoleic acid, eicosapentanoic acid, docosahexaneoic acid, and mixtures thereof.

Preferred hydroxy acids for inclusion in the cosmetic compositions of the invention include salicyclic acid, lactic acid, glycolic acid, malic acid, mandelic acid, ascorbic acid, ascorbyl phosphoric acid, hydroxycitric acid, hydroxytetronic acid, citric acid, aleuritic acid, ellagic acid, rosemarinic acid, chlorogenic acid, polysulfonic acid, hyaluronic acid and mixtures thereof.

Preferred vitamins for inclusion in the cosmetic compositions of the invention include Vitamin A, Retinol, Retinoic Acid, Tretinoin, a member of the Vitamin B group, Vitamin C, Vitamin D, Vitamin E, Vitamin K, a Carotene, Biotin, Folic Acid, a derivative of one or more of the foregoing vitamins and mixtures thereof.

Another useful ingredient for inclusion in the cosmetic compositions of the invention comprises trehalose and/or a cosmetically acceptable salt or ester thereof.

The cosmetic compositions of the invention may be formulated as a foam, lotion, mousse, solution, emulsion, cream, gel, pomade, balm, pump spray, stick, aerosol spray, ointment, paste, dermal patch and mixtures thereof. Typical products formulated from the cosmetic compositions of the invention include a shampoo, hair conditioner, styling mousse, hair treatment preparation, hair coloring preparation, semi-perm preparation, oxidation dye, body wash, bar soap, liquid soap, skin car preparation, lipstick, mascara, color cosmetic, nail care preparation, lip balm, skin cleansing preparation, moisturizing lotion, moisturizing cream, sunscreen lotion, sunscreen cream and mixtures thereof.

The following nonlimiting examples shall serve to illustrate the embodiments of this invention. Unless otherwise indicated to the contrary, all parts and percentages are on a weight basis.

EXAMPLE 1

Preparation of a Chelated Mineral Water

One kilogram of chelated mineral water was prepared by mixing for 15 minutes using a propeller mixer 986 g of mineral water obtained from Mount Clemens, Mich., US together with 14 g of Dissolvine® NA3[1]. The resultant chelated water was then utilized for the preparation of a mineral water masque composition in Example 2.

[1] Dissolvine® NA3 is a blend of the disodium and tetrasodium salts of ethylenediaminetetraacetic acid.

EXAMPLE 2

Preparation of a Mineral Water Masque Composition

One kilogram of a mineral water masque composition was prepared using the following ingredients:

| Ingredient | Amount |
|---|---|
| Chelated Mineral water from Example 1 | 779.00 g |
| ProLipid ® 151[2] | 70.00 g |
| Indopol ® H-100[3] | 28.00 g |
| Shea Butter Extract[4] | 42.00 g |
| Arlacel ® 165[5] | 70.00 g |
| OptiPhen ®[6] | 11.00 g |

[2] Prolipid ® 151 is a blend of stearic acid, behenyl alcohol, glyceryl stearate, stearyl alcohol, cetyl alcohol, palmitic acid, hydroxyethyl cetearamido-propyldimonium chloride and myristyl alcohol.
[3] Indopol ® H-100 is an isobutylene/butene copolymer.
[4] Shea Butter Extract is a fatty extract from the seed of the Shea tree
[5] Arlacel ® 165 is a mixture of glyceryl stearate and polyethylene glycol-100 stearate.
[6] OptiPhen ® is a blend of 2-phenoxyethanol, caprylyl glycol and an emollient base.

The chelated mineral water from Example 1 was heated to 80° C. and the five other ingredients were then mixed in the water while maintaining the temperature at 80° C. The mixture was then mixed with a Homo® mixer for 15 minutes and thereafter allowed to cool to room temperature.

It is to be understood that the foregoing detailed description of the invention is intended to illustrate and not limit the scope of the invention that is defined by the appended claims hereto.

What is claimed is:
1. A composition comprising mineral water obtained from Mount Clemens, Mich., US, said water comprising cations and anions present in the following amounts on the basis of grams per liter of water: calcium at 5 to 20 grams per liter; magnesium at 2 to 6 grams per liter; potassium at 0.5 to 3 grams per liter; iron at 1 to 4 grams per liter; sodium at 0.1 to 0.3 grams per liter; chloride at 50 to 200 grams per liter; sulfate at 1 to 2 grams per liter; and bromide at 0.4 to 0.8 grams per liter; and a chelating agent, wherein all of the minerals in the water are in solution.

2. The composition of claim 1 wherein the minerals in the mineral water are of cations selected from the group consisting of calcium, magnesium, iron, potassium and sodium and mixtures thereof, and of anions selected from the group consisting of chloride, sulfate, bromide and mixtures thereof.

3. The composition of claim 1 wherein the chelating agent comprises an ammonium and/or a sodium salt of an acid selected from the group consisting of ethylenediaminetetraacetic acid, nitrilotetraacetic acid, .beta.-alaninediacetic acid, ethylenediaminosuccinic acid, aminotrimethylenephosphoric acid, serinediaacetic acid, asparaginediacetic acid, methylgylcinediacetic acid and mixtures thereof.

4. The composition of claim 3 wherein the chelating agent comprises an ammonium and/or a sodium salt of ethylenediaminetetraacetic acid.

5. The composition of claim 3 wherein the chelating agent comprises a mixture of the disodium and the tetra sodium salts of ethylenediaminetetraacetic acid.

6. The composition of claim 3 wherein the chelating agent comprises a mixture of the ammonium, disodium and tetra-sodium salts of ethylenediaminetetraacetic acid.

7. The composition of claim 1 wherein the chelating agent is present in an amount of about 0.01 wt. % to about 20.0 wt. %, based on the weight of the composition.

8. The composition of claim 1 wherein the composition contains less than about 1 ppm of mercury or other heavy metals, less than about 1 ppm of cyanide, less than about 1 ppm of nitrite-nitrate and less than about 1 ppm of phenolics.

9. The composition of claim 1 further comprising a cosmetically acceptable monomeric or polymeric skin-conditioning agent, a cosmetically acceptable topical carrier and mixtures thereof.

10. The composition of claim 9 comprising an ingredient selected from the group consisting of an emollient; a lipid material; a film-former; an emulsifier; a humectant; a solvent; an optional co-solvent; a cationic surfactant; an anionic surfactant; an amphoteric surfactant; a zwitterionic surfactant; a cationic phospholipid; a hair-conditioning agent; an anti-inflammatory agent; a skin moisturizer; a skin exfoliant; a skin cleanser; a skin protectant; a silicone; a skin-soothing agent; a skin penetration agent; a skin-whitening agent; a solubilizing agent; an anesthetic; an analgesic; a hydroxy acid; an essential amino acid and/or an ester or salt thereof; an essential fatty acid and/or an ester or salt thereof; a hormone; a colorant and/or a dye; a thickener; a rheology control agent; a preservative; an insect repellant; a vitamin and/or pro-vitamin; a perfume and/or a fragrance; a plant extract; a flavorant; seed; crushed seed nut shells; silica; a clay; mica; beads; luffa particles; polyethylene balls; a pH adjusting agent; a processing flow agent; and mixtures thereof.

11. The composition of claim 10 wherein the lipid material comprises a shea butter extract.

12. The composition of claim 10 wherein the emulsifier comprises a stearate.

13. The composition of claim 10 wherein the hydroxy acid is selected from the group consisting of salicyclic acid, lactic acid, glycolic acid, malic acid, mandelic acid, ascorbic acid, ascorbyl phosphoric acid, hydroxycitric acid, hydroxytetronic acid, citric acid, aleuritic acid, ellagic acid, rosemarinic acid, chlorogenic acid, polysulfonic acid, hyaluronic acid and mixtures thereof.

14. The composition of claim 10 wherein the vitamin is selected from the group consisting of Vitamin A, Retinol, Retinoic Acid, Tretinoin, a member of the Vitamin B group, Vitamin C, Vitamin D, Vitamin E, Vitamin K, a Carotene, Biotin, Folic Acid, a derivative of one or more of the foregoing vitamins and mixtures thereof.

15. The composition of claim 1 further comprising an ingredient selected from the group consisting of butylated hydroxyanisole, butylated hydroxytoluene, propyl gallate, tert-butylhydroquinone, ascorbyl palmitate, capsaicin, reserbatol, linolenic acid, .gamma.-linolenic acid, linoleic acid, eicosapentanoic acid, docosahexaneoic acid, and mixtures thereof.

16. The composition of claim 1 further comprising trehalose and/or a cosmetically acceptable salt or ester thereof.

17. The composition of claim 1 that is formulated as a cosmetic composition wherein the chelated mineral water is present in the cosmetic composition in an amount of about 0.5 to about 76 wt. %, based on the weight of the cosmetic composition.

18. The composition of claim 17 wherein the cosmetic composition is formulated as a foam, lotion, mousse, solution, emulsion, cream, gel, pomade, balm, pump spray, stick, aerosol spray, ointment, paste, dermal patch and mixtures thereof.

19. The composition of claim 18 wherein the cosmetic composition is formulated for use as a shampoo, hair conditioner, styling mousse, hair treatment preparation, hair coloring preparation, semi-perm preparation, oxidation dye, body wash, bar soap, liquid soap, skin care preparation, lipstick, mascara, color cosmetic, nail care preparation, lip balm, skin cleansing preparation, moisturizing lotion, moisturizing cream, sunscreen lotion, sunscreen cream and mixtures thereof.

20. A cosmetic composition comprising the following components: (a) a mineral water, said mineral water comprising cations and anions present in the following amounts on the basis of grams per liter of water: calcium at 5 to 20 grams per liter; magnesium at 2 to 6 grams per liter; potassium at 0.5 to 3 grams per liter; iron at 1 to 4 grams per liter; sodium at 0.1 to 0.3 grams per liter; chloride at 50 to 200 grams per liter; sulfate at 1 to 2 grams per liter; and bromide at 0.4 to 0.8 grams per liter;

(b) a chelating agent;
(c) a cosmetically acceptable skin-conditioning agent; and
(d) a cosmetically acceptable topical carrier,
wherein all of the minerals in the water are in solution.

21. The composition of claim 20 wherein the minerals in the mineral water are of cations selected from the group consisting of calcium, magnesium, iron, potassium and sodium and mixtures thereof, and of anions selected from the group consisting of chloride, sulfate, bromide and mixtures thereof.

22. The composition of claim 20 wherein the mineral water is obtained from Mount Clemens, Mich., US.

23. The composition of claim 20 wherein the chelating agent comprises an ammonium and/or a sodium salt of an acid selected from the group consisting of ethylenediaminetetraacetic acid, nitrilotetraacetic acid, .beta.-alaninediacetic acid, ethylenediaminosuccinic acid, aminotrimethylenephosphoric acid, serinediaacetic acid, asparaginediacetic acid, methylgylcinediacetic acid and mixtures thereof.

24. The composition of claim 23 wherein the chelating agent comprises an ammonium and/or a sodium salt of ethylenediaminetetraacetic acid.

25. The composition of claim 24 wherein the chelating agent comprises a mixture of the disodium and the tetra sodium salts of ethylenediaminetetraacetic acid.

26. The composition of claim 20 wherein the chelating agent comprises a mixture of the ammonium, disodium and tetrasodium salts of ethylenediaminetetraacetic acid.

27. The composition of claim 20 wherein the chelating agent is present in an amount of about 0.01 wt. % to about 20.0 wt. %, based on the weight of component (a) plus component (b).

28. The composition of claim 20 wherein the composition contains less than about 1 ppm of mercury or other heavy metals, less than about 1 ppm of cyanide, less than about 1 ppm of nitrite-nitrate and less than about 1 ppm of phenolics.

29. The composition of claim 20 comprising an ingredient selected from the group consisting of an emollient; a lipid material; a film-former; an emulsifier; a humectant; a solvent; an optional co-solvent; a cationic surfactant; an anionic surfactant; an amphoteric surfactant; a zwitterionic surfactant; a cationic phospholipid; a hair-conditioning agent; an anti-inflammatory agent; a skin moisturizer; a skin exfoliant; a skin cleanser; a skin protectant; a silicone; a skin-soothing agent; a skin penetration agent; a skin-whitening agent; a solubilizing agent; an anesthetic; an analgesic; a hydroxy acid; an essential amino acid and/or an ester or salt thereof; an essential fatty acid and/or an ester or salt thereof; a hormone; a colorant and/or a dye; a thickener; a rheology control agent; a preservative; an insect repellant; a vitamin and/or pro-vitamin; a perfume and/or a fragrance; a plant extract; a flavorant; seed; crushed seed nut shells; silica; a clay; mica; beads; luffa particles; polyethylene balls; a pH adjusting agent; a processing flow agent; and mixtures thereof.

30. The composition of claim 29 wherein the lipid material comprises a shea butter extract.

31. The composition of claim 29 wherein the emulsifier comprises a stearate.

32. The composition of claim 29 wherein the hydroxy acid is selected from the group consisting of salicyclic acid, lactic acid, glycolic acid, malic acid, mandelic acid, ascorbic acid, ascorbyl phosphoric acid, hydroxycitric acid, hydroxytetronic acid, citric acid, aleuritic acid, ellagic acid, rosemarinic acid, chlorogenic acid, polysulfonic acid, hyaluronic acid and mixtures thereof.

33. The composition of claim 29 wherein the vitamin is selected from the group consisting of Vitamin A, Retinol, Retinoic Acid, Tretinoin, a member of the Vitamin B group, Vitamin C, Vitamin D, Vitamin E, Vitamin K, a Carotene, Biotin, Folic Acid, a derivative of one or more of the foregoing vitamins and mixtures thereof.

34. The composition of claim 20 further comprising an ingredient selected from the group consisting of butylated hydroxyanisole, butylated hydroxytoluene, propyl gallate, tert-butylhydroquinone, ascorbyl palmitate, capsaicin, reserbatol, linolenic acid, .gamma.-linolenic acid, linoleic acid, eicosapentanoic acid, docosahexaneoic acid, and mixtures thereof.

35. The composition of claim 20 further comprising trehalose and/or a cosmetically acceptable salt or ester thereof.

36. The composition of claim 20 wherein the mineral water is present in the cosmetic composition in an amount of about 0.5 to about 76 wt. %, based on the weight of the cosmetic composition.

37. The composition of claim 20 wherein the cosmetic composition is formulated as a foam, lotion, mousse, solution, emulsion, cream, gel, pomade, balm, pump spray, stick, aerosol spray, ointment, paste, dermal patch and mixtures thereof.

38. The composition of claim 20 wherein the cosmetic composition is formulated for use as a shampoo, hair conditioner, styling mousse, hair treatment preparation, hair coloring preparation, semi-perm preparation, oxidation dye, body wash, bar soap, liquid soap, skin car preparation, lipstick, mascara, color cosmetic, nail care preparation, lip balm, skin cleansing preparation, moisturizing lotion, moisturizing cream, sunscreen lotion, sunscreen cream and mixtures thereof.

\* \* \* \* \*